US011200670B2

(12) United States Patent
Maetschke et al.

(10) Patent No.: US 11,200,670 B2
(45) Date of Patent: Dec. 14, 2021

(54) REAL-TIME DETECTION AND CORRECTION OF SHADOWING IN HYPERSPECTRAL RETINAL IMAGES

(71) Applicant: International Business Machines Corporation, Armonk, NY (US)

(72) Inventors: Stefan Renard Maetschke, Ascot Vale (AU); Noel Faux, Melbourne (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/866,889

(22) Filed: May 5, 2020

(65) Prior Publication Data

US 2021/0350527 A1 Nov. 11, 2021

(51) Int. Cl.
*G06T 7/00* (2017.01)
*G06T 11/00* (2006.01)
*G06T 7/70* (2017.01)

(52) U.S. Cl.
CPC .............. *G06T 7/0012* (2013.01); *G06T 7/70* (2017.01); *G06T 11/00* (2013.01); *G06T 2207/30041* (2013.01)

(58) Field of Classification Search
CPC ......... G06T 7/0012; G06T 7/70; G06T 11/00; G06T 2207/30041
See application file for complete search history.

(56) References Cited

U.S. PATENT DOCUMENTS

| | | | | |
|---|---|---|---|---|
| 2004/0085542 | A1* | 5/2004 | Soliz | A61B 3/12 356/456 |
| 2005/0270486 | A1 | 12/2005 | Teiwes et al. | |
| 2010/0208951 | A1 | 8/2010 | Williams et al. | |
| 2011/0043756 | A1 | 2/2011 | Kahn et al. | |
| 2012/0065518 | A1* | 3/2012 | Mangoubi | G06T 7/0012 600/473 |

(Continued)

FOREIGN PATENT DOCUMENTS

| | | |
|---|---|---|
| CN | 201624637 U | 11/2010 |
| CN | 104463215 A | 3/2015 |

(Continued)

OTHER PUBLICATIONS

Dey, Nilanjan; "Uneven illumination correction of digital images: A survey of the state-of-the-art", Optik, vol. 183, pp. 483-495, Apr. 2019.

(Continued)

*Primary Examiner* — Syed Haider
(74) *Attorney, Agent, or Firm* — Cantor Colburn LLP; Joseph Petrokaitis (57) ABSTRACT

A method for real-time detection and correction of shadowing in hyperspectral retinal images may include capturing receiving, using a processor, a hyperspectral image of a retina of a patient, detecting, by the processor, a shadow in the hyperspectral image, determining, by the processor that the shadow of the hyperspectral image exceeds a threshold, and in response to determining that the shadow of the hyperspectral image exceeds the threshold, initiating, using the processor, a capture of an additional hyperspectral image of the retina of the patient. Various other methods, systems, and computer-readable media are also disclosed.

19 Claims, 7 Drawing Sheets

(56) References Cited

U.S. PATENT DOCUMENTS

| | | | |
|---|---|---|---|
| 2015/0110372 A1* | 4/2015 | Solanki | G16H 30/20 382/130 |
| 2016/0092721 A1 | 3/2016 | Kanagasingam et al. | |
| 2017/0124394 A1* | 5/2017 | Thavalengal | H04N 9/04515 |

FOREIGN PATENT DOCUMENTS

| | | |
|---|---|---|
| CN | 109410191 A | 1/2019 |
| CN | 106651899 B | 7/2019 |
| CN | 109730633 A | 10/2019 |

OTHER PUBLICATIONS

Furtado et al., "Segmentation of Eye Fundus Images by Density Clustering in Diabetic Retinopathy", IEEE EMBS International Conference on Biomedical & Health Informatics (BHI), Orlando, FL, pp. 25-28, 2017.

Mahapatra et al., "Retinal Image Quality Classification Using Saliency Maps and CNNs", Machine Learning in Medical Imaging, vol. 10019: Lecture Notes in Computer Science, pp. 172-179, 2016.

M'Hiri et al., "Quality Assessment of Retinal Hyperspectral Images Using SURF and Intensity Features", In: M. Descoteaux et al. (eds), Medical Image Computing and Computer-Assisted Intervention—MICCAI 2017, Lecture Notes in Computer Science, vol. 10434, pp. 118-125, 2017.

Rajanna et al., "Neural Networks with Manifold Learning for Diabetic Retinopathy Detection", (submitted on Dec. 12, 2016) pp. 1-6, https://arxiv.org/abs/1612.03961.

Schmitz-Valckenberg et al., "Semiautomated Image Processing Method for Identification and Quantification of Geographic Atrophy in Age-Related Macular Degeneration", Investigative Ophthalmology & Visual Science, Sep. 2011, vol. 52, pp. 7640-7646.

International Search Report; International Application No. PCT/IB2021/053515; International Filing Date: Apr. 28, 2021; dated Aug. 12, 2021; 8 pages.

* cited by examiner

REAL-TIME DETECTION AND CORRECTION OF SHADOWING IN HYPERSPECTRAL RETINAL IMAGES

BACKGROUND

The present disclosure relates in general to computer-based image analysis, and more specifically to computer systems configured and arranged to perform real time detection and correction of shadowing in hyperspectral retinal images.

Hyperspectral sensors can be used to capture image frames at specific wavelength lambdas (e.g. 900 nm to 450 nm in steps of 5 nm). Each image can represent a spectral band (e.g., narrow wavelength range of the electromagnetic spectrum), and the spectral bands can be combined to form a three-dimensional (x, y, λ) hyperspectral data shape (e.g., cube) for processing and analysis. The variables x and y can represent two spatial dimensions of the scene, and λ can represent the spectral dimension, which can include a range of wavelengths.

Known techniques for capturing retinal images with hyperspectral sensors suffer from various artefacts, such as shadowing due to uneven illumination or insufficient pupil dilation. Shadowing results in poor image quality that can necessitate shadowing correction or reacquisition of the retinal images. Unfortunately, conventional methods for shadow detection in retinal images captured by hyperspectral sensors do not provide results in real time. In instances where correction of the shadowing in an image is difficult, reacquisition of images in a clinical setting can be prohibitively time-consuming.

SUMMARY

According to one or more embodiments of the present disclosure, a method for real-time detection and correction of shadowing in hyperspectral retinal images includes receiving, using a processor, a hyperspectral image of a retina of a patient, detecting, by the processor, a shadow in the hyperspectral image, determining, by the processor that the shadow of the hyperspectral image exceeds a threshold, and in response to determining that the shadow of the hyperspectral image exceeds the threshold, initiating, using the processor, a capture of an additional hyperspectral image of the retina of the patient. Identifying shadowing and other artefacts in images enable the systems and methods described herein to correct and/or reacquire images in real-time to avoid wasting time in a clinical setting and increase accuracy in final images.

In one or more embodiments of the present invention, the method includes generating an alert to a user comprising a message indicating that new hyperspectral generating an alert to a user comprising a message indicating that new hyperspectral image of the retina are needed because of the shadow. Detecting the shadow in the hyperspectral image includes calculating a shift vector of the shadow in the hyperspectral image. The shift vector indicates an amount and angle of shadowing. Determining that the shadow of the hyperspectral image exceeds the threshold includes comparing the shift vector with the threshold.

In one or more embodiments of the present invention, the method includes detecting, by the processor, a field of view (FOV) and optic disk (OD) of the retina in the hyperspectral image, computing, by the processor, a soft mask using the FOV and the OD of the retina in the hyperspectral image, computing, by the processor, a first center of gravity using the soft mask and the hyperspectral image, normalizing, by the processor, the hyperspectral image, applying, by the processor, a tensor to the normalized hyperspectral image, computing, by the processor, a second center of gravity using the normalized hyperspectral image with the applied tensor, and generating, by the processor, the shift vector using the first center of gravity and the second center of gravity. In some examples, the method includes detecting, by the processor, a second shadow in the additional hyperspectral image, determining, by the processor, that the second shadow of the additional hyperspectral image does not exceed the threshold, and in response to determining that the second shadow of the additional hyperspectral image does not exceed the threshold, transmitting, by the processor, the hyperspectral image and the additional hyperspectral image, wherein the hyperspectral image comprises an overlay of the shadow and values of the shift vector.

The technical solutions can also be implemented by a system, a computer program product, an apparatus, a machine, a device, or in other practical applications in one or more embodiments of the present invention.

Additionally, in one or more embodiments of the present invention, a method for real-time detection and correction of shadowing in hyperspectral retinal images includes receiving, using a processor, a hyperspectral image of a retina of a patient, detecting, by the processor, a shadow in the hyperspectral image by calculating a shift vector of the hyperspectral image, determining, by the processor, the shift vector of the hyperspectral image exceeds a threshold, and in response to determining that the shift vector of the hyperspectral image exceeds the threshold, facilitating an image sensor to capture an additional hyperspectral image of the retina of the patient. The shift vector is indicative of an amount and angle of shadowing. Identifying shadowing and other artefacts in images reduces time-consuming re-acquisition of images in a clinical setting and increases accuracy in the final images.

Additionally, in one or more embodiments of the present disclosure, a method for real-time detection and correction of shadowing in hyperspectral retinal images includes receiving, using a processor, hyperspectral images of a retina of a patient, registering, by the processor, the hyperspectral image to correct a detected eye motion between the hyperspectral images, detecting, by the processor, a shadow in the registered hyperspectral images, determining, by the processor, that the shadow of the hyperspectral images exceeds a threshold, and in response to determining that the shadow of the hyperspectral images exceeds the threshold, facilitating an image sensor to capture an additional hyperspectral image of the retina of the patient. Detecting the shadow in the hyperspectral images includes calculating a shift vector of the shadow in the hyperspectral images. Real-time identification of poor image quality in captured images enables systems and methods described herein to quickly correct and/or require images in a clinical setting.

Additional technical features and benefits are realized through the techniques of the present disclosure. Embodiments and aspects of the disclosure are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the disclosure are apparent from the following detailed description taken in conjunction with the accompanying drawings in which:

The diagrams depicted herein are illustrative. There can be many variations to the diagrams, or the operations described therein, without departing from the spirit of the disclosure. For instance, the actions can be performed in a differing order or actions can be added, deleted or modified. Also, the term "coupled," and variations thereof, describe having a communications path between two elements and do not imply a direct connection between the elements with no intervening elements/connections between them. All of these variations are considered a part of the specification.

DETAILED DESCRIPTION

Exemplary embodiments of the present disclosure relate to, among other things, devices, systems, methods, computer-readable media, techniques, and methodologies for real-time shadow detection and correction in hyperspectral images. Hyperspectral imaging devices includes a hyperspectral image sensor and a processor used to facilitate image storage, processing and visualization. The image sensor captures image frames at different wavelengths and the resulting data may be an ordered collection of frames.

Capturing retinal images using hyperspectral imaging devices results in images that include various artefacts, such as shadowing due to uneven illumination or insufficient pupil dilation of the patient. The presence of shadowing in the retinal images can result in poor image quality, which necessitates the captured retinal images being rejected and needing to be reacquired and/or correcting the shadowing of the captured images. Conventional methods for shadow detection are slow (e.g., non-real time), which make the re-acquisition of images in a clinical setting time-consuming. Additionally, conventional methods do not provide a readily available tool for real-time correction of shadowing detected in hyperspectral retinal images.

The systems and methods described herein are directed to real-time shadow detection that are used to trigger a real-time re-acquisition of images deemed insufficient due to poor quality resulting from detected shadowing in the images. Conventional methods for image reacquisition can take several seconds and shadow detection takes additional time, which increases the time burden in a clinical environment. Real-time shadow detection (and correction) and reacquisition of images reduces the time it takes to obtain accurate and reliable images, which translates to an overall cost savings. Additionally, because more and higher quality images can be captured during a shorter timeframe, doctors and technicians can make more accurate diagnosis, resulting in better patient outcomes. Further, the system can provide additional information (e.g., angle and offset for correction of shadowing) generated during the shadow detection with the newly acquired images, which provides context and be used to more accurately make a diagnosis using the images. The system can detect a shadow and/or other image regions that are of different brightness than the retina due to artefacts of the image, such as an optic disc or other retinal organ.

In some exemplary examples, the hyperspectral camera or image sensor of a hyperspectral imaging device captures images of a retina of a patient. The images are registered (e.g., aligned) to correct for eye motion between scans. The system then processes the registered images and detect a field of view (FOV) of the retina and retinal features, such as an optic disc (OD) of the retina. Using the FOV and detected retinal features, the system computes and/or generates a soft mask. The soft mask is a weight-tensor used to obscure features of the image to ensure accuracy in accurate detection of shadowing in the images. The soft mask is used to obtain a shift vector of the hyperspectral images. The shift vector includes at least two values, which indicates an amount of shadowing and direction (e.g., angle) of the shadowing detected in the hyperspectral images. Shadow correction of the hyperspectral images is performed by weighing the image pixel under the soft mask, as indicated by the shift vector. The system uses the shift vector to determine whether to reacquire hyperspectral images. For example, the system compares the value of the shift vector to a predetermined threshold. If the value of the shift vector exceeds the predetermine threshold, new images are automatically acquired. Upon acquiring the new images, the original image and the new images are presented to the doctor or technician. In some embodiments, the original images can be augmented with an overlay that presents the data generated during the shadow detection (e.g., shift vector, retinal features, etc.) prior to presenting the images to the doctor or technician.

Although described within the context of capturing retinal images, the systems and methods described herein are applicable to any device, scenario, and/or field that utilizes hyperspectral imaging and requires reacquisition of images due to artefacts or quality issues of the initially captured images.

Figure 1A:
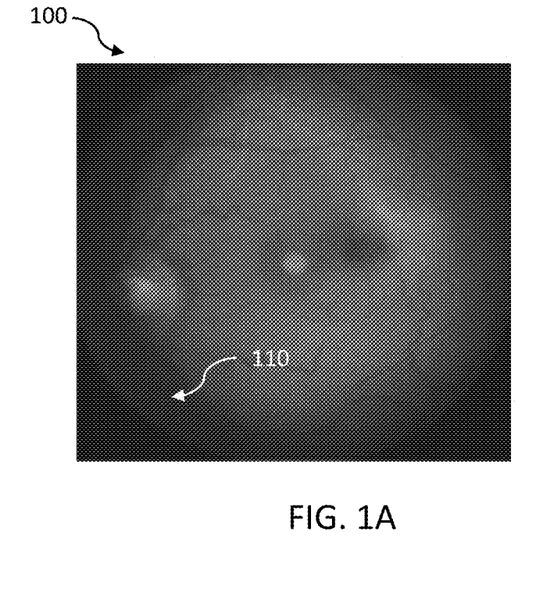
FIG. 1A shows an example retinal image captured by hyperspectral sensors in accordance with one or more embodiments of the present disclosure.
Figure 1B:
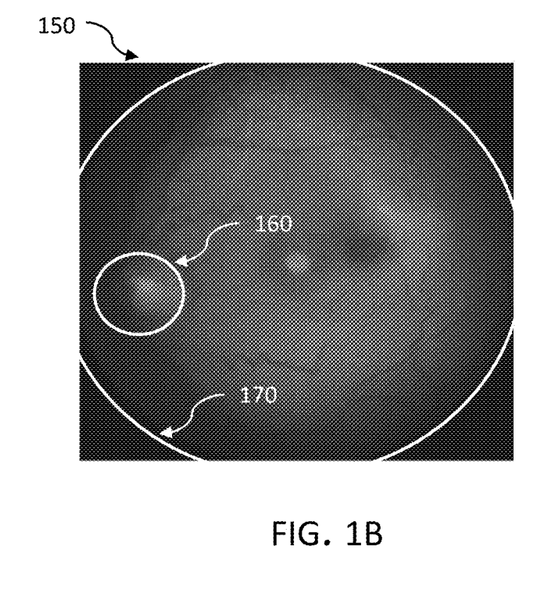
FIG. 1B shows an example retinal image captured by hyperspectral sensors in accordance with one or more embodiments of the present disclosure.

Referring now to FIG. 1A, an example retinal image 100 captured by a hyperspectral sensor is depicted in accordance with one or more embodiments of the present disclosure. The image depicts a single frame in a retinal hyperspectral image. One or more artefacts, such as a shadow 110, is present in the hyperspectral retinal image. Shadowing can be the result of uneven illumination of the pupil and/or insufficient pupil dilation of the patient. FIG. 1B depicts an example retinal image 150 displaying the field of view (FOV) 170 and the optic disc (OD) 160 of the retina of the patient. In some embodiments, the FOV 170 refers to the portion of the retina that is visible through the hyperspectral camera or sensor at a specified position and orientation. Objects outside of the FOV 170 are not captured in the retinal imaging. The OD 160 refers to a small blind spot in an eye that is the point where axons of retinal ganglion cells come together. The OD 160 appears as a bright spot in an image of a retina.

Figure 2:
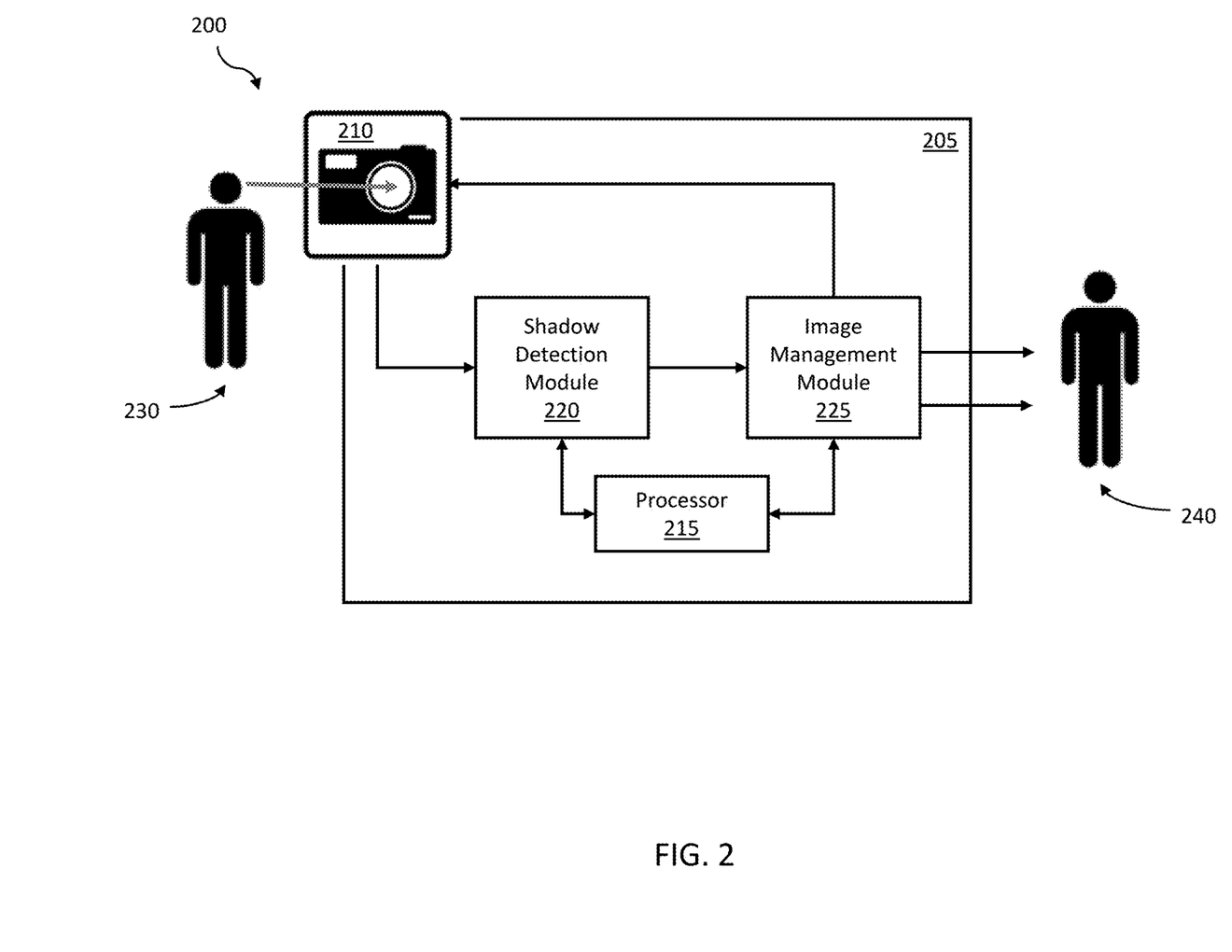
FIG. 2 is a schematic hybrid data flow/block diagram illustrating real-time shadow detection and correction in hyperspectral images in accordance with one or more example embodiments of the present disclosure.

FIG. 2 is a schematic hybrid data flow/block diagram illustrating a data flow 200 for real-time shadow detection and correction in hyperspectral images in an imaging device in accordance with one or more example embodiments of the present disclosure. In some examples, an image sensor 210 of an imaging device 205 can be used to capture an image 100 of a retina of a patient 230. The image sensor 210 can be any type of imagining device capable of capturing an image 100 of a retina. Examples of an image sensor 210 include a hyperspectral device or camera for retinal imaging. Hyperspectral cameras capture image frames at specific wavelengths (e.g., 900 nm to 450 nm in steps of 5 nm) and the resulting data is an ordered collection of frames or a three-dimensional (x, y, λ) hyperspectral data shape used for processing and analysis, where x and y represent two spatial dimensions of the scene, and λ represents the spectral dimension, which includes a range of wavelengths. An example of the imaging device 205 is a hyperspectral device for retinal imaging, such as a Metabolic Hyperspectral Retinal Camera (MHRC), which includes an image sensor 210 and a processor for image storage, processing and visualization. Although the image sensor 210 is depicted as an integrated component of the imaging device 205, in some embodiments, the image sensor 210 is an external component in communication with the imaging device 205.

The images captured by the image sensor 210 are transmitted to a shadow detection module 220 coupled to a physical processor 215 of the imaging device 205. The physical processor 215 can generally represent any type or form of hardware-implemented processing unit capable of interpreting and/or executing computer-readable instructions. In one example, the physical processor 215 accesses and/or modifies one or more of the modules (e.g., shadow detection module 220 and/or image management module 225) stored in memory. Additionally, or alternatively, the physical processor 215 executes one or more of the modules to perform real-time shadow detection and correction in hyperspectral images. Examples of the physical processor 215 include, without limitation, microprocessors, microcontrollers, Central Processing Units (CPUs), Graphical Processing Units (GPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

The images captured by the image sensor 210 are processed, by the shadow detection module 220, to detect shadowing in the images in real-time. In some examples, the shadow detection module 220 detects a shadow 110 in the images and transmits the data associated with the shadow 110 to the image management module 225 of the imaging device 205. The image management module 225, coupled with the processor 215, compares the data associated with the shadow 110 with a predetermined threshold. In some examples, the predetermined threshold is set manually by a user of the imaging device 205 or can be dynamically set and/or adjusted based on previous actions of a user while using the imaging device 205, such as a technician or doctor 240. If the image management module 225 determines that the data associated with the detected shadow 110 exceeds the predetermined threshold, the image management module 225 triggers an action in real-time. Examples of the action include, but are not limited to, automatically facilitating re-acquisition of hyperspectral images of the retina of the patient 230 and alerting the technician or doctor 240 that due to insufficient quality detected in the image caused by shadowing, new images need to be obtained. In some examples, the action includes alerting the technician or doctor 240 prior to initiating re-acquisition of the images and requesting confirmation to proceed with the re-acquisition.

In response to the image management module 225 triggering a real-time action due to shadowing detected in the hyperspectral image, the processor 215 initiates the image sensor 210 to capture new hyperspectral images of the retina of the patient 230. The images are transmitted to the shadow detection module 220 for processing. The image management module 225 receives the data generated by the shadow detection module 220 for any shadowing detected in the new hyperspectral images of the retina of the patient 230 and determines that data associated with the detected shadowing in the new hyperspectral images do not exceed the predetermined threshold. The image management module 225 transmits the original hyperspectral images and the new hyperspectral images of the retina of the patient 230 to the doctor 240. In some examples, the original hyperspectral images are augmented with the information associated with the shadowing (e.g., location and/or amount of the shadowing detected in the image).

The imaging device 205 can execute multiple iterations of image reacquisition in order to obtain images that are satisfactory (e.g., does not exceed the threshold) to transmit to the doctor 240. In some examples, the imaging device 205 has a limit (e.g., manually set and/or automatically determined) that limits the number of iterations of image reacquisition. Upon reaching the limit and not having captured satisfactory images, the image management module 225 can generate and transmit a message to the doctor 240 that satisfactory images could not be captured. The message can include an indication of the number of attempts to acquire images, one or more sets of the previously acquired images, and/or possible reasons why the images were of poor quality or otherwise insufficient.

In some examples, images captured by the imaging device 205 are stored in a datastore, either local in the imaging device 205 and/or external to the imaging device 205 (e.g., cloud storage, remote storage device, etc.).

Figure 3:
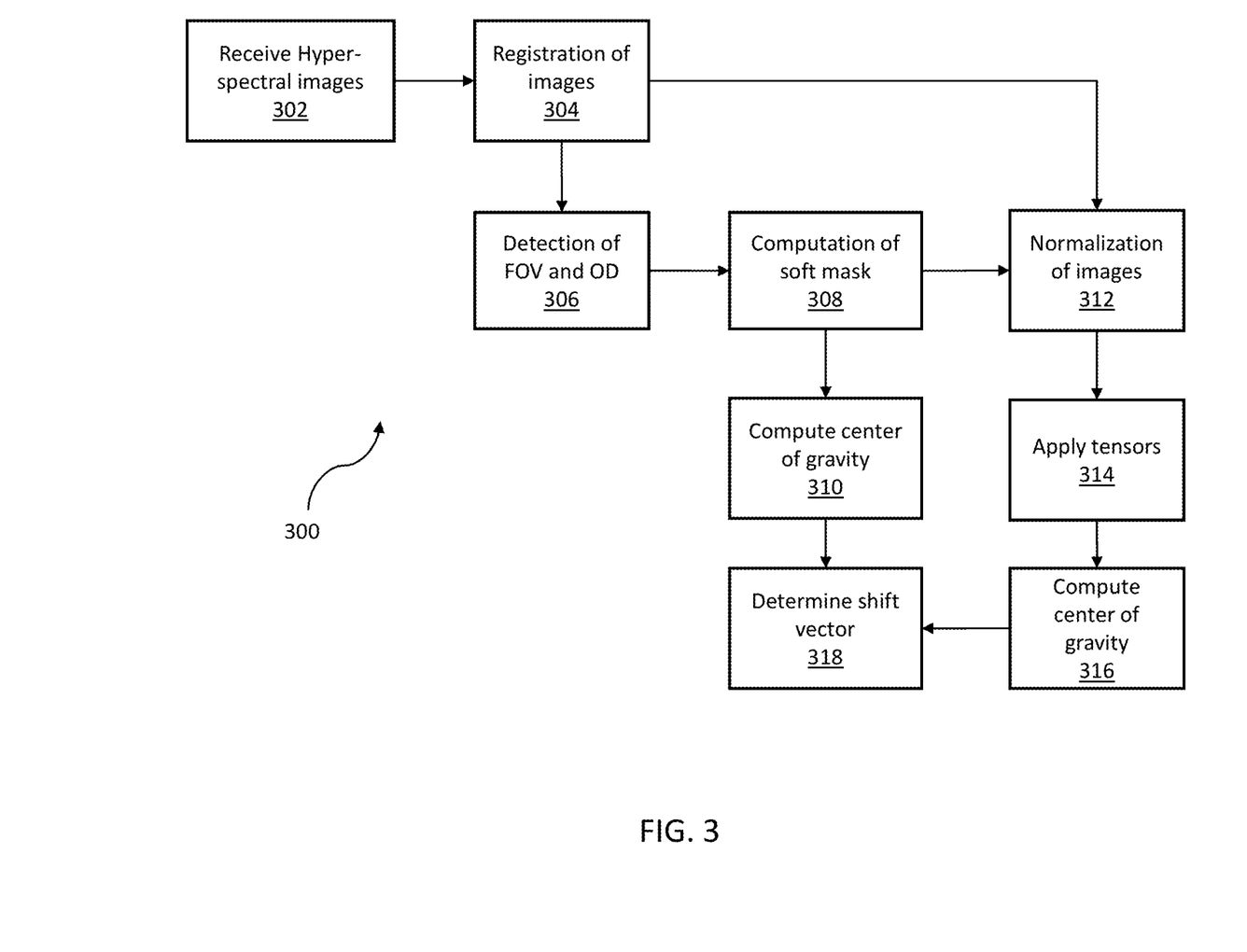
FIG. 3 is a schematic hybrid data flow/block diagram illustrating shadow detection in hyperspectral retinal images in accordance with one or more example embodiments of the present disclosure.

FIG. 3 is a schematic hybrid data flow/block diagram illustrating a process 300 for shadow detection in hyperspectral retinal images. In accordance with embodiments of the invention, the process 300 is performed by a computer-based system, including, for example, the data flow 200 (shown in FIG. 2). At block 302, an image sensor, such as image sensor 210, of a retinal imaging device, such as imaging device 205, captures hyperspectral images of a retina of a patient 230. The captured images can be taken at different wavelengths and stored as an ordered collection of frames. At block 304, the captured images are registered. For example, the captured images are registered by the shadow detection module 220. The images are registered, for example, to correct for eye motion between scans of the retina. The images are registered using any known technique and/or algorithm for registering hyperspectral images. In some examples, registration of images can include alignment of the frames of the hyperspectral images using spatial information contained in the images and spectral information from when the images were taken at different wavelengths. At block 306, the shadow detection module 220 processes the registered images and detects different components of the images, such as the FOV 170 of the image, and retinal features in the images, such as the OD 160.

Now referring to block 308, the shadow detection module 220 may compute a soft mask for the image. The soft mask is computed using the detected FOV 170 and OD 160 or other relevant retinal organs. The soft mask is a weight-tensor that can be used to obscure the detected components of the images that may hinder or otherwise negatively affect use of the images for diagnostic purposes. At block 310, the shadow detection module 220 uses the soft mask to compute a center of gravity of the soft mask. In some examples, the center of gravity of the soft mask may be calculated by using any known technique or algorithm to calculate a center of gravity for an image or component, such as the soft mask. For example, the center of gravity of the soft mask can be calculated by performing computations on the computed soft mask, such as averaging the soft mask row and column-wise.

Now referring to block 312, the shadow detection module 220 normalizes the registered images from block 304. In some embodiments, the shadow detection module 220 multiplies the registered images from block 304 element-wise with the calculated soft mask from block 308 and then frame-wise normalizes the images (e.g., weighted pixels of frame sum to equal 1). At block 314, one or more tensors are applied to the normalized images from block 312. For example, the weighted (with the soft mask) and normalized images from block 312 are multiplied element-wise with row and column coordinate tensors. At block 316, the images with the applied tensors are used to compute the center of gravity within the weighted image. Any known techniques or algorithms for computing a center of gravity can be applied to the weighted image to derive a center of gravity. At block 318, the shift vector can be calculated. In some examples, the center of gravity from block 316 and the center of gravity from block 310 are used to calculate the shift vector. The shift vector is computed by computing the element-wise difference between the center of gravity of the soft mask and the center of gravity of the weighted image.

The shift vector includes at least two values. In some examples, the shift value includes a length value that is indicative of the amount of shadowing in an image. The shift vector also includes a direction (e.g., angle) value that indicates the location of the shadow in the image. In some examples, the shadow detection module 220 uses the shift vector, such as the shift vector calculated at block 318, to detect a shadow in the image. Shadow detection is performed by comparing the length value of the shift vector to an established, predetermined threshold. Shadow correction is performed by the shadow detection module 220 by shifting a ring-shaped weight mask (e.g., diameter same as FOV 170) as indicated by the shift vector and multiplying the image frame by the weight mask.

Figure 4A:
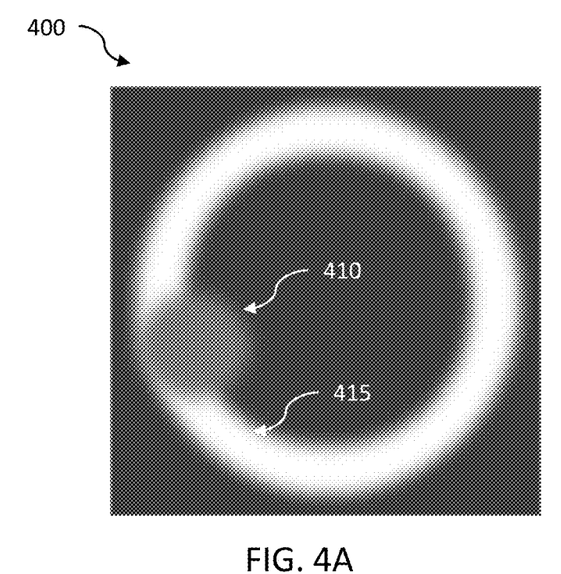
FIG. 4A is an example retinal image displaying a soft mask generated during shadow detection in hyperspectral retinal images according to one or more embodiments of the present disclosure.
Figure 4B:
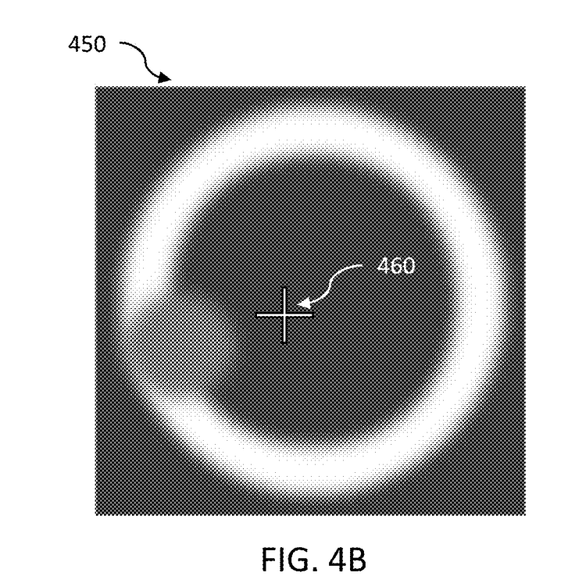
FIG. 4B is an example retinal image displaying the center of gravity of the soft mask generated during shadow detection in hyperspectral retinal images according to one or more embodiments of the present disclosure.

Now referring to FIG. 4A, a soft mask 400 generated during shadow detection in hyperspectral retinal images. The soft mask 400 is a weight-tensor generated by the shadow detection module 220 using data obtained from the hyperspectral images (e.g., FOV and/or OD measurements) and used for shadow correction. The soft mask 400 is used to obscure artefacts and characteristics of the retina that may hinder or otherwise negatively affect use of the images for diagnostic purposes. For example, component 410 is a portion of the soft mask 400 generated to obscure the OD 160 detected in the original hyperspectral images while component 415 is a portion of the soft mask 400 generated to obscure the shadow 110 detected in the original hyperspectral images. FIG. 4B depicts an image 450 that displays a center of gravity 460 of the soft mask 400 calculated by the shadow detection module 220. The center of gravity 460 of the soft mask is used to calculate a shift vector, which is used by the image management module 225 to determine whether to re-acquire new hyperspectral images of the retina of the patient 230.

Figure 5A:
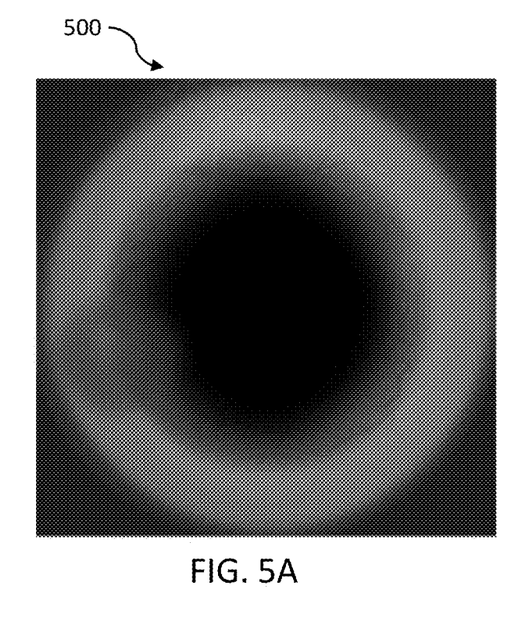
FIG. 5A is an example retinal image weighted with the soft mask generated during the shadow detection according to one or more embodiments of the present disclosure
Figure 5B:
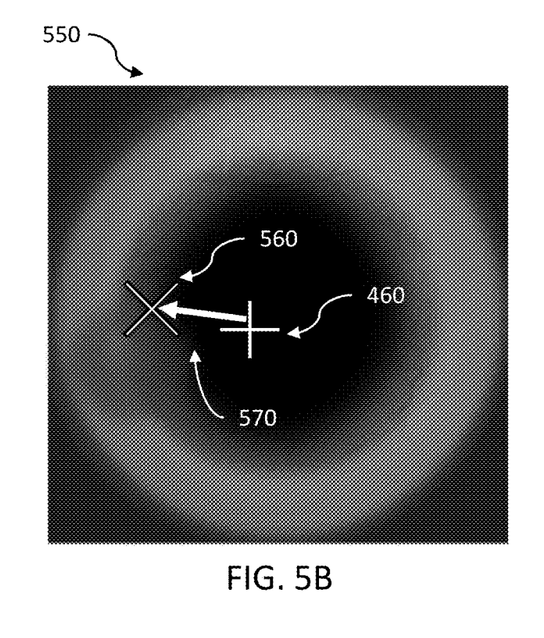
FIG. 5B is an example retinal image with an overlay with data generated during shadow detection according to one or more embodiments of the present disclosure.

Now referring to FIG. 5A, an image (or frame) 500 from a collection of hyperspectral images captured by an image sensor 210 is depicted. The image 500 is weighted or corrected with the soft mask 400 calculated by the shadow detection module 220, as described in FIG. 3. FIG. 5B is an image or frame 550 from a hyperspectral image of the retina of a patient 230. The image 550 includes an overlay of information generated by the shadow detection module 220. For example, the image 550 includes the soft mask center of gravity 460, the weighted image center of gravity 560, and the shift vector 570 indicative of the size and direction of the shadowing in the original hyperspectral image. The information is provided to the doctor 240 or technician to aid them in the use of the images for diagnostic purposes.

Figure 6:
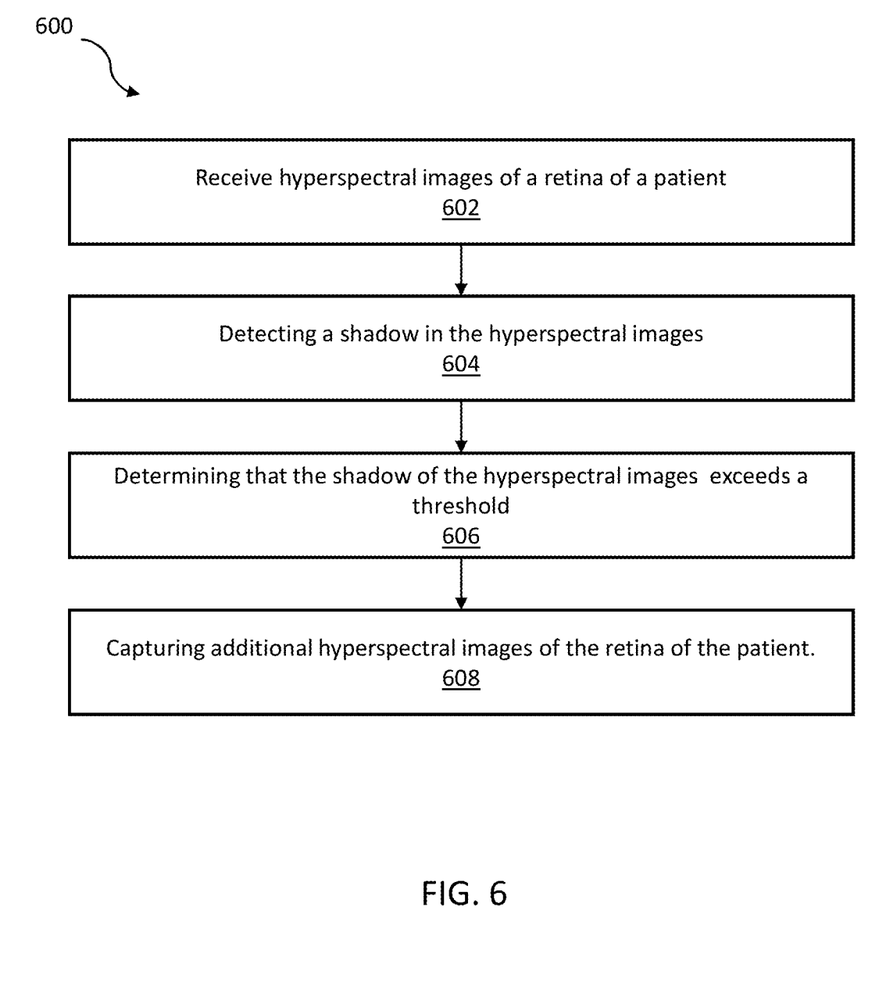
FIG. 6 is a process flow diagram of an illustrative method for detecting and correcting shadowing in hyperspectral retinal images in accordance with one or more example embodiments of the present disclosure.

Illustrative methods in accordance with example embodiments of the disclosure and corresponding data structures (e.g., modules, units, and other such components) for performing the methods are now described. It should be noted that each operation of the method 600 depicted in FIG. 6 are performed by one or more of the modules or the like described herein. These modules can be implemented in any combination of hardware, software, and/or firmware as described herein. In certain example embodiments, one or more of these modules can be implemented, at least in part, as software and/or firmware modules that include computer-executable instructions that when executed by a processing circuit cause one or more operations to be performed. A system or device described herein as being configured to implement example embodiments can include one or more processing circuits, each of which may include one or more processing units or nodes. Computer-executable instructions can include computer-executable program code that when executed by a processing unit can cause input data contained in or referenced by the computer-executable program code to be accessed and processed to yield output data.

FIG. 6 is a flow diagram of an example computer-implemented method 600 for providing real-time shadow detection and correction in hyperspectral images. The steps shown in FIG. 6 can be performed by any suitable computer-executable code and/or computing system. In one example, each of the steps shown in FIG. 6 can represent an algorithm whose structure includes and/or is represented by multiple sub-steps, examples of which will be provided in greater detail below.

As illustrated in FIG. 6, at step 602 one or more of the systems described herein receives hyperspectral images of a retina of a patient. The systems described herein can perform step 602 in any suitable manner. For example, the image sensor 210 of an imaging device 205 captures hyperspectral images of a retina of a patient. As discussed herein, the image sensor 210 can be any type of hyperspectral sensor capable of taking images at different wavelengths, which can be combined to form a three-dimensional (x, y, λ) hyperspectral data shape for processing and analysis, where x and y represent two spatial dimensions of the scene, and λ represents the spectral dimension, which includes a range of wavelengths.

At step 604, one or more of the systems described herein detect a shadow in the hyperspectral images. The systems described herein can perform step 604 in any suitable manner. For example, the shadow detection module 220 of the imaging device 205 detects a shadow 110 in the hyperspectral images captured by the image sensor 210.

In some examples, the frames of the hyperspectral images captured at step 602 are registered. The shadow detection module 220 executes or facilitates registration (e.g., alignment) of the captured images. The images are registered to correct and/or compensate for variations in the frames, such as for correcting eye motion of the patient between scans. Using the registered images, the shadow detection module 220 processes the images to detect and identify different components and retinal features, such as the FOV 170 of the image, the OD 160 of the retina, and the like.

In some examples, a soft mask 400 is computed by the shadow detection module 220 using the components and features identified from the images. The soft mask 400 is a weight-tensor used to obscure features of the images which can hinder accurate diagnosis or contribute to poor quality of the image.

Using the calculated soft mask 400, as described in FIG. 3, the shadow detection module 220 computes a center of gravity 460 of the soft mask. The shadow detection module then multiplies, element-wise, the soft mask and the registered images and then, frame-wise, normalizes the images. The shadow detection module 220 applies one or more tensors to the normalized and weighted images and uses the resulting images to calculate a center of gravity 560 for the weighted, normalized images. The shadow detection module 220 then computes or generates the shift vector 570 using the center of gravity 560 of the weighted, normalized images and the center of gravity 460 of the soft mask 400. The shift vector 570 includes at least two values, a length and an angle. The length indicates the amount of shadowing and the angle of the shift vector indicates the location of the shadow 110 in the image.

At step 606, one or more of the systems described herein determines that the shadow of the hyperspectral images exceeds a threshold. The systems described herein can perform step 606 in any suitable manner. For example, the image management module 225 of the imaging device 205 determines that the shadow 110 of the hyperspectral images exceeds a threshold.

In some examples, the image management module 225 receives the shift vector 570 computed by the shadow detection module 220. The image management module 225 compares at least one value of the shift vector, such as the length value with an identified threshold. In some examples, the threshold can be manually entered by a technician or doctor using the imaging device 205. The threshold may be a value stored in a profile associated with the technician or doctor using the device and can be different for each individual. The threshold can be a global value that is applied to all images captured by the imaging device 205. In some examples, the threshold can include multiple components. The threshold can be a conditional or multi-part threshold which can specify different actions for different values. For example, the threshold can indicate that if a shift vector value falls within a first range, shadow correction can be applied and if the shift vector value falls within a second range, new images need to be acquired.

At step 608, one or more of the systems described herein can initiating the capturing of additional hyperspectral images of the retina of the patient. The systems described herein can perform step 608 in any suitable manner. For example, the image management module 225 of the imaging device 205 can facilitate capturing additional hyperspectral images of the retina of the patient in response to determining that the shadow of the hyperspectral images exceeds the threshold.

In some examples, the image management module 225 determines that the shift vector value does not exceed the threshold, in which case the images are transmitted to the doctor without further processing or any additional action.

In some examples, the image management module 225 determines that the length value of the shift vector falls within a range of a threshold that requires shadow correction, the image management module 225 facilitates shadow correction of the image. In some examples, shadow correction is performed by shifting a ring-shaped weighted soft mask (e.g., diameter same as FOV) as indicated by the shift vector and multiplying the image frame by the weighted mask. The shadow corrected image is then processed by the shadow detection module 220 to calculate a new shift vector. The image management module 225 uses the values from the new shift vector to determine whether the shadow corrected image is sufficient to transmit to the doctor, or if new images need to be acquired despite the shadow correction.

In some examples, if the value of the shift vector exceeds the threshold or falls within a range of the threshold indicating that new images need to be acquired, the image management module 225 generates a message to the technician or doctor, indicating that new images are needed and requesting instructions regarding whether to obtain new images. The imaging device 205 receives an indication from the technician or doctor. If the indication is to not acquire new images, the original images are transmitted to the technician or doctor with a note indicating that new images are recommended. In some examples, if the indication is to acquire new images, the image management module 225, in response to receiving the indication from the user, facilitates a new iteration of acquiring and processing new images.

In some examples, the image management module 225 determines that the length value of the shift vector exceeds a predetermined threshold or falls within a range of a threshold indicating that new images need to be acquired. The image management module 225 automatically initiates reacquisition of the images (e.g., facilitating new images being acquired by the image sensor 210). The image management module 225 also generates and transmits an alert to the doctor or technician, indicating that new images are being acquired. The alert indicates why new images are being acquired. The new images are then processed by the shadow detection module 220, which generates a new shift vector for the newly acquired images. The image management module 225 uses the new shift vector to determine whether the newly acquired images are of sufficient quality to transmit to the doctor or technician or if reacquisition of images is again required.

If the new images are satisfactory (e.g., does not exceed the threshold), the new images are transmitted to the doctor or technician. In some examples, the old images are also transmitted to the doctor or technician. The old images are transmitted in their original state and/or can be augmented with data generated by the shadow detection module 220, such as the shift vector, the identified components (e.g., FOV, OD, etc.), location and size of the shadow, center of gravity of the soft mask, center of gravity of the weighted, normalized image, or the like. The additional data provides additional context for the doctor or technician to use with the images for diagnostic purposes.

In some examples, the systems and methods described herein execute multiple iterations of image acquisition and processing to capture satisfactory images. The imaging device utilizes a limit to restrict the number of iterations of the process to avoid unduly burdening the system and wasting time. The limit can be set manually by a user of the imaging device 205 or can be dynamically determined based on the quality of the images. For example, if the shift vector of each set of acquired images remains within an identified range for a certain number of image acquisitions, the system can determine that satisfactory images are not able to be captured at this time. The image management module 225 generates a message to the doctor or technician indicating that image re-acquisition is not recommended. The message indicates the number of attempts of reacquisitions and data indicating that the images are of poor quality. In some examples, the message includes the previously captured images, or a subset of the previously captured images, and/or includes links to access such data, which may be stored in a datastore, either local to the imaging device 205 or stored remotely.

In some example embodiments, a method for real-time detection and correction of shadowing in hyperspectral retinal images includes receiving, using a processor, a hyperspectral image of a retina of a patient; detecting, by the processor, a shadow in the hyperspectral image by calculating a shift vector of the hyperspectral image; determining, by the processor, the shift vector of the hyperspectral image exceeds a threshold; and in response to determining that the shift vector of the hyperspectral image exceeds the threshold, facilitating, by the processor, an image sensor to capture an additional hyperspectral image of the retina of the patient. The shift vector includes a length of the shadow and an angle of the shadow.

In another example embodiment, a method for real-time detection and correction of shadowing in hyperspectral retinal images includes receiving, using a processor, hyperspectral images of a retina of a patient; registering, by the processor, the hyperspectral image to correct a detected eye motion between the hyperspectral images; detecting, by the processor, a shadow in the registered hyperspectral images; determining, by the processor, that the shadow of the hyperspectral images exceeds a threshold; and in response to determining that the shadow of the hyperspectral images exceeds the threshold, facilitating, by the processor, an image sensor to capture an additional hyperspectral image of the retina of the patient. Detecting the shadow in the hyperspectral images includes calculating a shift vector of the shadow in the hyperspectral images.

Figure 7:
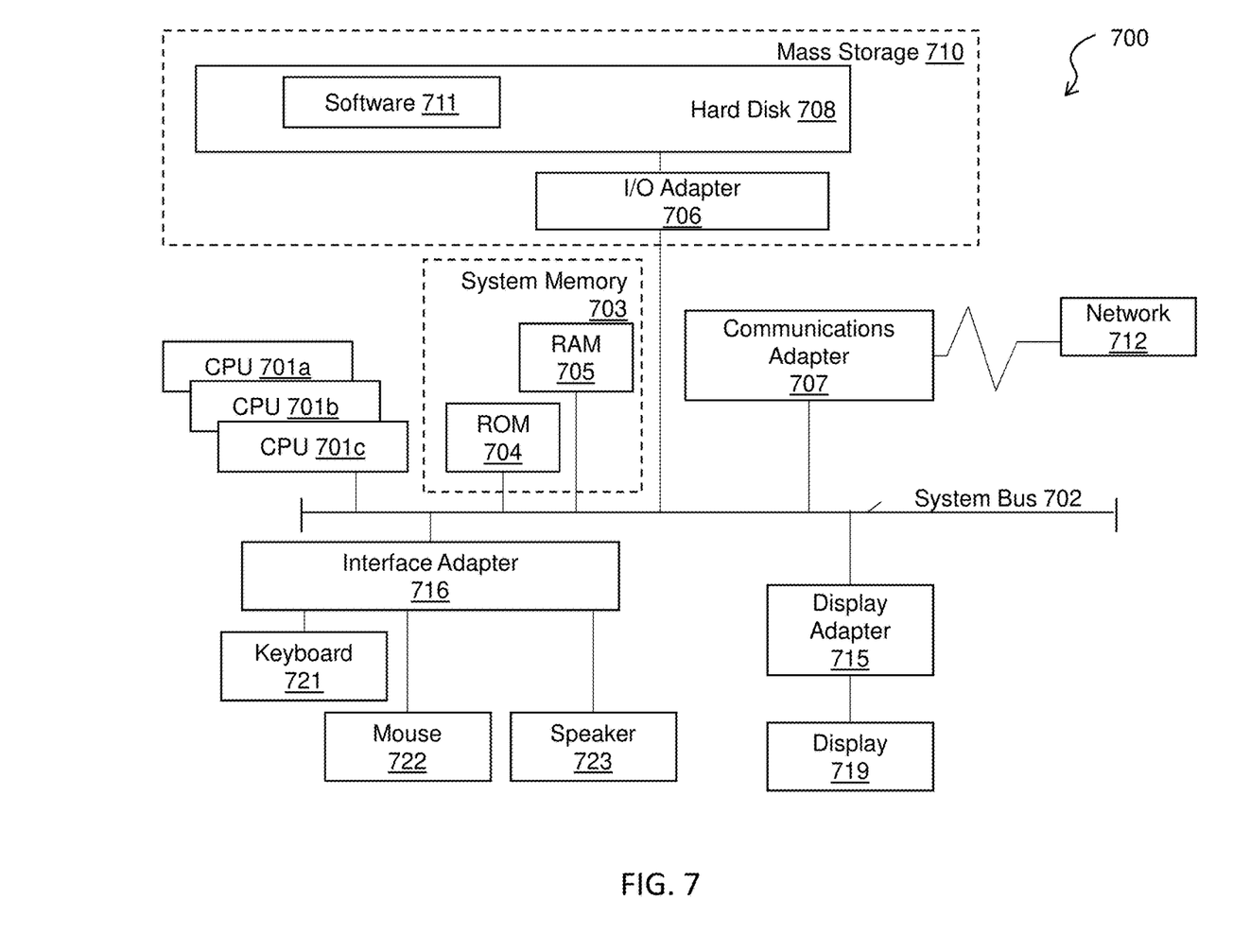
FIG. 7 depicts a computer system according to one or more embodiments of the present disclosure.

Turning now to FIG. 7, a computer system 700 is generally shown in accordance with an embodiment of the present invention. The computer system 700 can be an electronic, computer framework comprising and/or employing any number and combination of computing devices and networks utilizing various communication technologies, as described herein. The computer system 700 can be easily scalable, extensible, and modular, with the ability to change to different services or reconfigure some features independently of others. The computer system 700 may be, for example, a server, desktop computer, laptop computer, tablet computer, or smartphone. In some examples, computer system 700 may be a cloud computing node. Computer system 700 may be described in the general context of computer system executable instructions, such as program modules, being executed by a computer system. Generally, program modules may include routines, programs, objects, components, logic, data structures, and so on that perform particular tasks or implement particular abstract data types. Computer system 700 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, the computer system 700 has one or more central processing units (CPU(s)) 701a, 701b, 701c, etc. (collectively or generically referred to as processor(s) 701). The processors 701 can be a single-core processor, multi-core processor, computing cluster, or any number of other configurations. The processors 701, also referred to as processing circuits, are coupled via a system bus 702 to a system memory 703 and various other components. The system memory 703 can include a read only memory (ROM) 704 and a random-access memory (RAM) 705. The ROM 704 is coupled to the system bus 702 and may include a basic input/output system (BIOS), which controls certain basic functions of the computer system 700. The RAM is read-write memory coupled to the system bus 702 for use by the processors 701. The system memory 703 provides temporary memory space for operations of said instructions during operation. The system memory 703 can include random access memory (RAM), read only memory, flash memory, or any other suitable memory systems.

The computer system 700 comprises an input/output (I/O) adapter 706 and a communications adapter 707 coupled to the system bus 702. The I/O adapter 706 may be a small computer system interface (SCSI) adapter that communicates with a hard disk 708 and/or any other similar component. The I/O adapter 706 and the hard disk 708 are collectively referred to herein as a mass storage 710.

Software 711 for execution on the computer system 700 may be stored in the mass storage 710. The mass storage 710 is an example of a tangible storage medium readable by the processors 701, where the software 711 is stored as instructions for execution by the processors 701 to cause the computer system 700 to operate, such as is described herein below with respect to the various Figures. Examples of computer program product and the execution of such instruction is discussed herein in more detail. The communications adapter 707 interconnects the system bus 702 with a network 712, which may be an outside network, enabling the computer system 700 to communicate with other such systems. In one embodiment, a portion of the system memory 703 and the mass storage 710 collectively store an operating system, which may be any appropriate operating system, such as the z/OS or AIX operating system from IBM Corporation, to coordinate the functions of the various components shown in FIG. 7.

Additional input/output devices are shown as connected to the system bus 702 via a display adapter 715 and an interface adapter 716 and. In one embodiment, the adapters 706, 707, 715, and 716 may be connected to one or more I/O buses that are connected to the system bus 702 via an intermediate bus bridge (not shown). A display 719 (e.g., a screen or a display monitor) is connected to the system bus 702 by a display adapter 715, which may include a graphics controller to improve the performance of graphics intensive applications and a video controller. A keyboard 721, a mouse 722, a speaker 723, etc. can be interconnected to the system bus 702 via the interface adapter 716, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 7, the computer system 700 includes processing capability in the form of the processors 701, and, storage capability including the system memory 703 and the mass storage 710, input means such as the keyboard 721 and the mouse 722, and output capability including the speaker 723 and the display 719.

In some embodiments, the communications adapter 707 can transmit data using any suitable interface or protocol, such as the internet small computer system interface, among others. The network 712 may be a cellular network, a radio network, a wide area network (WAN), a local area network (LAN), or the Internet, among others. An external computing device may connect to the computer system 700 through the network 712. In some examples, an external computing device may be an external webserver or a cloud computing node.

It is to be understood that the block diagram of FIG. 7 is not intended to indicate that the computer system 700 is to include all of the components shown in FIG. 7. Rather, the computer system 700 can include any appropriate fewer or additional components not illustrated in FIG. 7 (e.g., additional memory components, embedded controllers, modules, additional network interfaces, etc.). Further, the embodiments described herein with respect to computer system 700 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source-code or object code written in any combination of one or more programming languages, including an object-oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instruction by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other devices to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

What is claimed is:

1. A computer-implemented method comprising:
   receiving, using a processor, a hyperspectral image of a retina of a patient;
   detecting, by the processor, a shadow in the hyperspectral image, wherein detecting the shadow in the hyperspectral image comprises calculating a shift vector of the shadow in the hyperspectral image;
   determining, by the processor that the shadow of the hyperspectral image exceeds a threshold by comparing the shift vector with the threshold; and
   in response to determining that the shadow of the hyperspectral image exceeds the threshold, initiating, by the processor, a capture of an additional hyperspectral image of the retina of the patient.

2. The computer-implemented method of claim 1 further comprising generating an alert to a user comprising a message indicating that new hyperspectral image of the retina are needed because of the shadow.

3. The computer-implemented method of claim 1, wherein the shift vector indicates an amount and angle of shadowing.

4. The computer-implemented method of claim 1 further comprising:
   detecting, by the processor, a field of view (FOV) and optic disk (OD) of the retina in the hyperspectral image;
   computing, by the processor, a soft mask using the FOV and the OD of the retina in the hyperspectral image;
   computing, by the processor, a first center of gravity using the soft mask and the hyperspectral image;
   normalizing, by the processor, the hyperspectral image;
   applying, by the processor, a tensor to the normalized hyperspectral image;

computing, by the processor, a second center of gravity using the normalized hyperspectral image with the tensor; and generating, by the processor, the shift vector using the first center of gravity and the second center of gravity.

5. The computer-implemented method of claim 1 further comprising:

detecting, by the processor, a second shadow in the additional hyperspectral image;

determining, by the processor, that the second shadow of the additional hyperspectral image does not exceed the threshold; and in response to determining that the second shadow of the additional hyperspectral image does not exceed the threshold, transmitting, by the processor, the hyperspectral image and the additional hyperspectral image, wherein the hyperspectral image comprises an overlay of the shadow and values of the shift vector.

6. A system comprising:

an image sensor;

a memory; and a processor coupled with the image sensor and the memory, the processor configured to perform a method comprising:

receiving a hyperspectral image of a retina of a patient;

detecting a shadow in the hyperspectral image, wherein detecting the shadow in the hyperspectral image comprises calculating a shift vector of the shadow in the hyperspectral image;

determining that the shadow of the hyperspectral image exceeds a threshold by comparing the shift vector with the threshold; and in response to determining that the shadow of the hyperspectral image exceeds the threshold, initiating a capture of an additional hyperspectral image of the retina of the patient by the image sensor.

7. The system of claim 6, wherein the method performed by the processor further comprises generating an alert to a user comprising a message indicating that a new hyperspectral image of the retina are needed because of the shadow.

8. The system of claim 6, wherein the shift vector indicates an amount and angle of shadowing.

9. The system of claim 6, wherein the method performed by the processor further comprises:

detecting a field of view (FOV) and optic disk (OD) of the retina in the hyperspectral image;

computing a soft mask using the FOV and the OD of the retina in the hyperspectral image;

computing a first center of gravity using the soft mask and the hyperspectral image;

normalizing the hyperspectral image;

applying a tensor to the normalized hyperspectral image;

computing a second center of gravity using the normalized hyperspectral image with the tensor; and generating the shift vector using the first center of gravity and the second center of gravity.

10. The system of claim 6, wherein the method performed by the processor further comprises:

detecting a second shadow in the additional hyperspectral image;

determining that the second shadow of the additional hyperspectral image does not exceed the threshold; and in response to determining that the second shadow of the additional hyperspectral image does not exceed the threshold, transmitting the hyperspectral image and the additional hyperspectral image, wherein the hyperspectral image comprises an overlay of the shadow and values of the shift vector.

11. A computer program product comprising a computer-readable storage media having computer-executable instructions stored thereupon, which when executed by a processor cause the processor to perform a method comprising:

receiving a hyperspectral image of a retina of a patient;

detecting a shadow in the hyperspectral image, wherein detecting the shadow in the hyperspectral image comprises calculating a shift vector of the shadow in the hyperspectral image;

determining that the shadow of the hyperspectral image exceeds a threshold by comparing the shift vector with the threshold; and in response to determining that the shadow of the hyperspectral image exceeds the threshold, facilitating an image sensor to capture an additional hyperspectral image of the retina of the patient.

12. The computer program product of claim 11, wherein the method performed by the processor further comprises generating an alert to a user comprising a message indicating that a new hyperspectral image of the retina are needed because of the shadow.

13. The computer program product of claim 11, wherein the shift vector indicates an amount and angle of shadowing.

14. The computer program product of claim 11, wherein the method performed by the processor further comprises:

detecting a field of view (FOV) and optic disk (OD) of the retina in the hyperspectral image;

computing a soft mask using the FOV and the OD of the retina in the hyperspectral image;

computing a first center of gravity using the soft mask and the hyperspectral image;

normalizing the hyperspectral image;

applying a tensor to the normalized hyperspectral image;

computing a second center of gravity using the normalized hyperspectral image with the tensor; and generating the shift vector using the first center of gravity and the second center of gravity.

15. The computer program product of claim 11, wherein the method performed by the processor further comprises:

detecting a second shadow in the additional hyperspectral image;

determining that the second shadow of the additional hyperspectral image does not exceed the threshold; and in response to determining that the second shadow of the additional hyperspectral image does not exceed the threshold, transmitting the hyperspectral image and the additional hyperspectral image, wherein the hyperspectral image comprises an overlay of the shadow and values of the shift vector.

16. A computer-implemented method comprising:

receiving, using a processor, a hyperspectral image of a retina of a patient;

detecting, by the processor, a shadow in the hyperspectral image by calculating a shift vector of the hyperspectral image;

determining, by the processor, the shift vector of the hyperspectral image exceeds a threshold by comparing the shift vector with the threshold; and in response to determining that the shift vector of the hyperspectral image exceeds the threshold, initiating, using the processor, a capture of an additional hyperspectral image of the retina of the patient.

17. The computer-implemented method of claim 16, wherein the shift vector comprises a length of the shadow and an angle of the shadow.

18. A computer-implemented method comprising:
- receiving, using a processor, hyperspectral images of a retina of a patient;
- registering, by the processor, the hyperspectral images to correct a detected eye motion between the hyperspectral images;
- detecting, by the processor, a shadow in the registered hyperspectral images, wherein detecting the shadow in the hyperspectral image comprises calculating a shift vector of the shadow in the hyperspectral image;
- determining, by the processor, that the shadow of the hyperspectral images exceeds a threshold by comparing the shift vector with the threshold; and
- in response to determining that the shadow of the hyperspectral images exceeds the threshold, initiating, using the processor, a capture of an additional hyperspectral image of the retina of the patient.

19. The computer-implemented method of claim 18, wherein detecting the shadow in the hyperspectral images comprises calculating a shift vector of the shadow in the hyperspectral images.

* * * * *